(12) United States Patent
Hung

(10) Patent No.: US 12,150,807 B2
(45) Date of Patent: Nov. 26, 2024

(54) SOUND DETECTING DEVICE FOR PELVIC FLOOR MUSCLE EXERCISE

(71) Applicant: Chien-Hsiung Hung, Myau-Li County (TW)

(72) Inventor: Chien-Hsiung Hung, Myau-Li County (TW)

(73) Assignee: WOMEN'S GUARD BIOMEDICAL TECHNOLOGY CORP., Taichung (TW)

( * ) Notice: Subject to any disclaimer, the term of this patent is extended or adjusted under 35 U.S.C. 154(b) by 274 days.

(21) Appl. No.: 17/969,748

(22) Filed: Oct. 20, 2022

(65) Prior Publication Data

US 2023/0145949 A1  May 11, 2023

(30) Foreign Application Priority Data

Nov. 10, 2021  (TW) ................. 110213254

(51) Int. Cl.
*A61B 7/04* (2006.01)

(52) U.S. Cl.
CPC ........ *A61B 7/04* (2013.01); *A61B 2562/0204* (2013.01)

(58) Field of Classification Search
CPC ........... A61B 7/04; A61B 2562/0204
See application file for complete search history.

(56) References Cited

U.S. PATENT DOCUMENTS

| 10,933,236 | B2 * | 3/2021 | Kang | A61N 1/36007 |
| 11,938,077 | B2 * | 3/2024 | Leivseth | A61H 19/40 |
| 2003/0220589 | A1 * | 11/2003 | Leivseth | A63B 23/20 600/591 |
| 2010/0087757 | A1 * | 4/2010 | Hoffman | A61B 5/0538 601/46 |
| 2016/0166833 | A1 * | 6/2016 | Oh | A61H 19/40 607/3 |

FOREIGN PATENT DOCUMENTS

WO  WO-2017035951 A1 *  3/2017  .......... A61N 1/0514

* cited by examiner

*Primary Examiner* — David L Ton

(57) ABSTRACT

A sound detecting device for pelvic floor muscle exercise includes: a main body, having a base seat; a sound collecting chamber, having an opening; an elastic sound receiving membrane, disposed in the main body and located at the opening; a support ring, disposed at a top end of the main body, arranged at a periphery of the elastic sound receiving membrane and corresponding to an outer periphery of the opening; a microphone, disposed at a bottom end of the sound collecting chamber; and an electric circuit board, disposed on the base seat, used for providing a wave filtering function and an amplifying function, connected to the microphone, and connected to at least one smart device installed with an application program (APP) through a Bluetooth device. As such, low frequencies generated when the pelvic floor muscle is relaxed or contacted can be amplified and precisely collected.

9 Claims, 9 Drawing Sheets

SOUND DETECTING DEVICE FOR PELVIC FLOOR MUSCLE EXERCISE

BACKGROUND OF THE INVENTION

1. Field of the Invention

The present invention relates to a detecting device, especially to a sound detecting device for pelvic floor muscle exercise capable of receiving low frequencies generated when the pelvic floor muscle is contracted and relaxed.

2. Description of Related Art

For strengthening the resilience of the urethral sphincter for improving urinary incontinence and improving frequent urination, urgent urination, urine leaking and nocturia, the Kegel exercise is necessary and a detection for ensuring whether the exercise being accurate is also required to be provided; a conventional detecting device is to use electrodes being adhered at an outer side of a location to be detected, or to use an inserting type device 9 having a rod member 91, which is used for detections, being inserted in a private part, for example a vagina 82, of a human body (as shown in FIG. 9, which is a schematic view showing an operating status of the conventional inserting type device); however, whether using the electrodes or the inserting type device having the rod member require to be in contact with an inner part or an outer part of the human body, thus the detecting operation may not be performed when the user wears an outfit or a skirt, and may not be used at any time desired by the user; moreover, the detecting operation is required to be performed in a private place or a room, and the detecting device requires to be in contact with the human body thereby possibly causing the private part of the human body to be infected, and the detection may not be precise when the placing location is incorrect; in addition, the structure of a stethoscope is used for listening the sounds of a heart or lungs in the whole world, a contacting part thereof contacting to human is made of a hard material such as plastic and formed as a planar surface for being served to collecting sounds, because the stethoscope itself is not provided with a membrane and a supporter, the stethoscope has to be operated by a doctor to collect and listen the active sound of the heart or the lungs though the hard plastic plate; however, the plastic plate made of the hard material and formed as the planar surface cannot be used for detecting the low frequencies generated when the pelvic floor muscle is contracted or relaxed, especially the pelvic floor muscle is located at an inner part of the human body. Accordingly, the practicability is very much limited, and the shortages existed in the prior art shall be improved by the skilled people in the art.

SUMMARY OF THE INVENTION

For solving the shortages existed in the prior art, one primary objective of the present invention is to provide a sound detecting device for pelvic floor muscle exercise, in which the interior and the top end of a main body are respectively disposed with a base seat, a sound collecting chamber, an elastic sound receiving membrane, a support ring, a microphone and an electric circuit board, for solving the shortages existed in the prior art.

Another objective of the present invention is to provide a sound detecting device for pelvic floor muscle exercise, in which an elastic sound receiving membrane is downwardly pressed through the pressure supplied by the skin muscle weight for being in a recessed status so as to be tightly adjacent to an outer side of skin or an outfit or a skirt and a sound collecting chamber is used for amplifying, thus the low frequencies generated through the vibrations caused by the pelvic floor muscle being contracted and relaxed can be collected with a more precise effect, and a Bluetooth device is used for transferring to a smart device installed with an application program (APP).

One another objective of the present invention is to provide a sound detecting device for pelvic floor muscle exercise, which has advantages of satisfies the ergonomics and conveniently operated without the needs of the electrodes and being inserted in a human part.

The problem to be solved by the present invention is that: for strengthening the resilience of the urethral sphincter for improving urinary incontinence and improving frequent urination, urgent urination, urine leaking and nocturia, the Kegel exercise is necessary and a detecting device for ensuring whether the exercise being accurate is to use electrodes being adhered at an outer side of a location to be detected, or to use an inserting type device having a rod member, which is used for detections, being inserted in a private part; however, whether using the electrodes or the inserting type device having the rod member require to be in contact with an inner part or an outer part of the human body, thus the detecting operation may not be performed when the user wears an outfit or a skirt, and may not be used at any time desired by the user; moreover, the detecting operation is required to be performed in a private place or a room, and the detecting device requires to be in contact with the human body thereby possibly causing the private part of the human body to be infected, and the detection may not be precise when the placing location is incorrect; in addition, the structure of a stethoscope is that a contacting part thereof contacting to human skin is made of a hard material such as plastic and formed as a planar surface for being served to collecting the sounds of a heart or lungs; however, the plastic plate made of the hard material and formed as the planar surface cannot be used for detecting the low frequencies generated when the pelvic floor muscle is contracted or relaxed, especially the pelvic floor muscle is located at an inner part of the human body. Accordingly, the operation is inconvenient and the practicability is very much limited.

For achieving the aforesaid objectives, one technical solution provided by the present invention is to provide a sound detecting device for pelvic floor muscle exercise, applied to receive low frequencies generated when the pelvic floor muscle is relaxed and contracted, characterized in that: including:
  a main body, having a base seat disposed therein and used for supporting;
  a sound collecting chamber, disposed in the main body and used for amplifying and collecting sounds for increasing the sensibility, wherein an opening having a sound receiving function is formed at a top end of the sound collecting chamber;
  an elastic sound receiving membrane, disposed in the main body and located at the opening of the sound collecting chamber, wherein the elastic sound receiving membrane covers on at a desired detecting location of an outer skin layer or an outfit or a skirt where the lower frequencies generated when the pelvic floor muscle is relaxed or contracted;
  a support ring, disposed at a top end of the main body, arranged at a periphery of the elastic sound receiving membrane and corresponding to an outer periphery of the opening of the sound collecting chamber, wherein a center of the support ring is formed with a middle hole allowing the elastic sound receiving membrane to be exposed;

a microphone, disposed at a bottom end of the sound collecting chamber; and an electric circuit board, disposed on the base seat, used for providing a wave filtering function and an amplifying function, and connected to the microphone;

wherein, the elastic sound receiving membrane is downwardly pressed through a pressure supplied by the skin muscle weight for being in a recessed status so as to be tightly adjacent to the skin or the outfit or the skirt, thus the low frequencies generated through the vibrations caused by the pelvic floor muscle being contracted and relaxed are able to be amplified and precisely collected.

Wherein, according to the present invention, a bottom end of the base seat of the main body is disposed with at least one anti-skid sound isolating pad used for avoiding displacements.

Wherein, according to the present invention, a shape of the elastic sound receiving membrane includes, but not limits to, an arc-shaped surface or a curved surface.

Wherein, according to the present invention, a material of which the elastic sound receiving membrane is made is a soft material.

Wherein, according to the present invention, a material of which the support ring is made includes, but not limits to, a metal material or a plastic material.

Wherein, according to the present invention, a top end of the support ring is additionally disposed with at least one accessory unit including, but not limiting to, an infrared unit or a magnet unit which is used for soothing the pelvic floor muscle and blood circulation.

Wherein, according to the present invention, the base seat is disposed with at least one vibrating motor which enables the main body to vibrate, massages the pelvic floor muscle and is connected to the electric circuit board, and at least one press button used for controlling the vibrating motor is disposed at an outer side of the main body and connected to the electric circuit board.

Wherein, according to the present invention, a top end of the main body is disposed with a charging light, a Bluetooth light, a switch light and a power switch which are connected to the electric circuit board; a charging hole is formed for a purpose of charging electricity, at least one battery connected to the electric circuit board is disposed in the main body.

Wherein, according to the present invention, the electric circuit board is used for providing a functional operating function and a received sound data transferring function through being connected to at least one smart device installed with an application program (APP) via a Bluetooth device.

Advantages achieved by the present invention are as follows: The interior and the top end of the main body are respectively disposed with the base seat, the sound collecting chamber, the elastic sound receiving membrane, the support ring, the microphone and the electric circuit board; as such, the elastic sound receiving membrane is downwardly pressed through the pressure supplied by the skin muscle weight for being in a recessed status so as to be tightly adjacent to the outer side of the skin or the outfit or the skirt and the sound collecting chamber is used for amplifying, thus the low frequencies generated through the vibrations caused by the pelvic floor muscle being contracted and relaxed can be collected with a more precise effect, and the Bluetooth device is used for transferring to the smart device installed with the application program (APP); moreover, the device provided by the present invention satisfies the ergonomics and can be conveniently operated without the needs of the electrodes and being inserted in the human part. Accordingly, the present invention is novel, more practical in use and satisfies the requirements of the users.

BRIEF DESCRIPTION OF CODES (Conventional)
- 82: Vagina
- 9: Inserting type device
- 91: Rod member (Present Invention)
- 1: Main body
- 10: Battery
- 101: Power switch
- 102: Charging light
- 103: Bluetooth light
- 104: Switch light
- 11: Changing hole
- 2: Base seat
- 21: Anti-skid sound isolating pad
- 3: Sound collecting chamber
- 31: Opening
- 32: Support ring
- 321: Middle hole
- 33: Accessory unit
- 34: Vibrating motor
- 341: Press button
- 4: Elastic sound receiving membrane
- 5: Microphone
- 6: Electric circuit board
- 7: Smart device
- 71: Application program (APP)
- 8: Thigh
- 81: Perineum

DETAILED DESCRIPTION OF THE PREFERRED EMBODIMENT

One preferred embodiment of the present invention will be described with reference to the drawings for illustrating the structural assembly, the technical means and the functions to be achieved by the present invention; and the actual ratios and the arrangement of components shall not be limited by the ratios and the arrangement of components in the provided figures.

Figure 1:
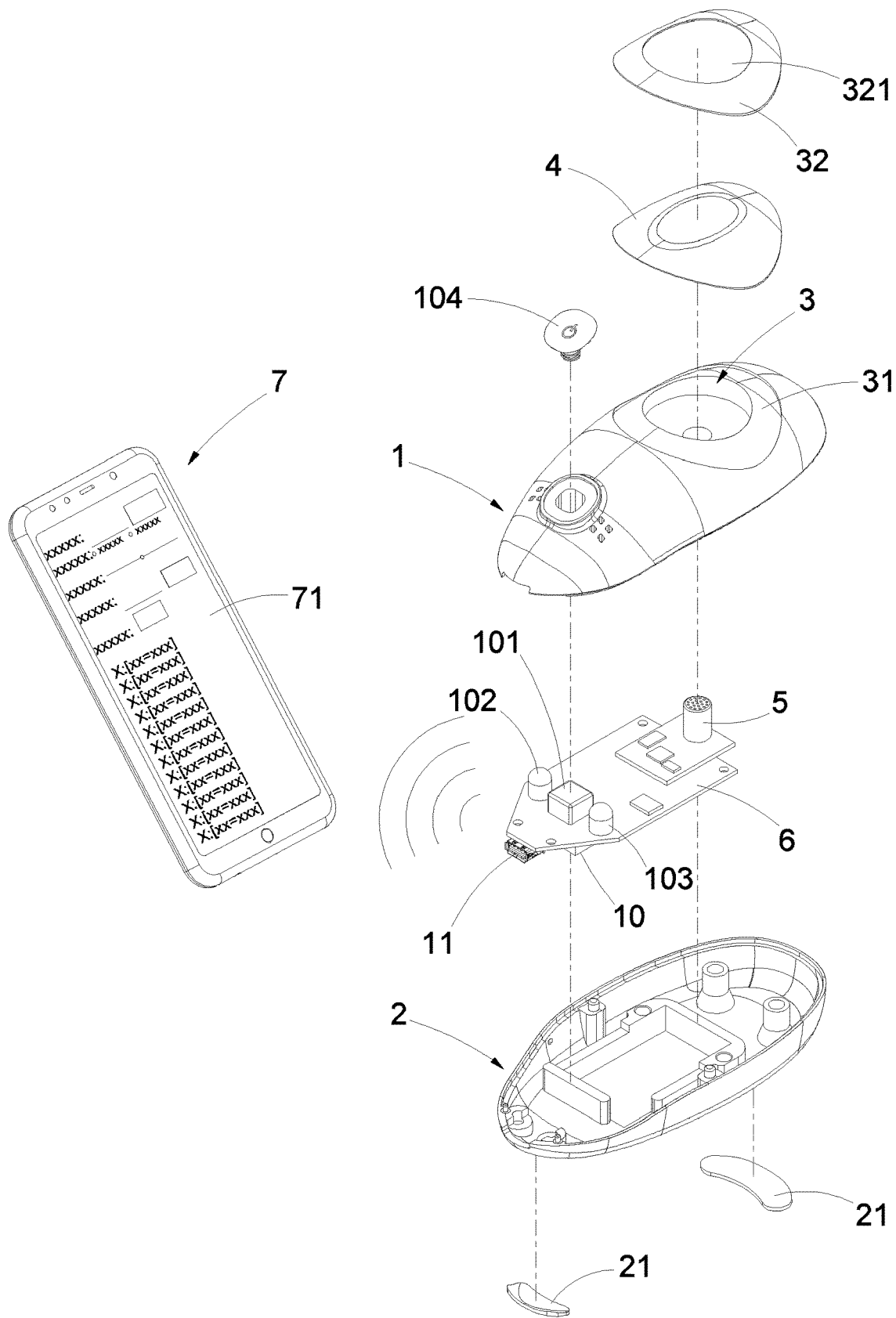
FIG. 1 is a perspective exploded view according to the present invention.
Figure 2:
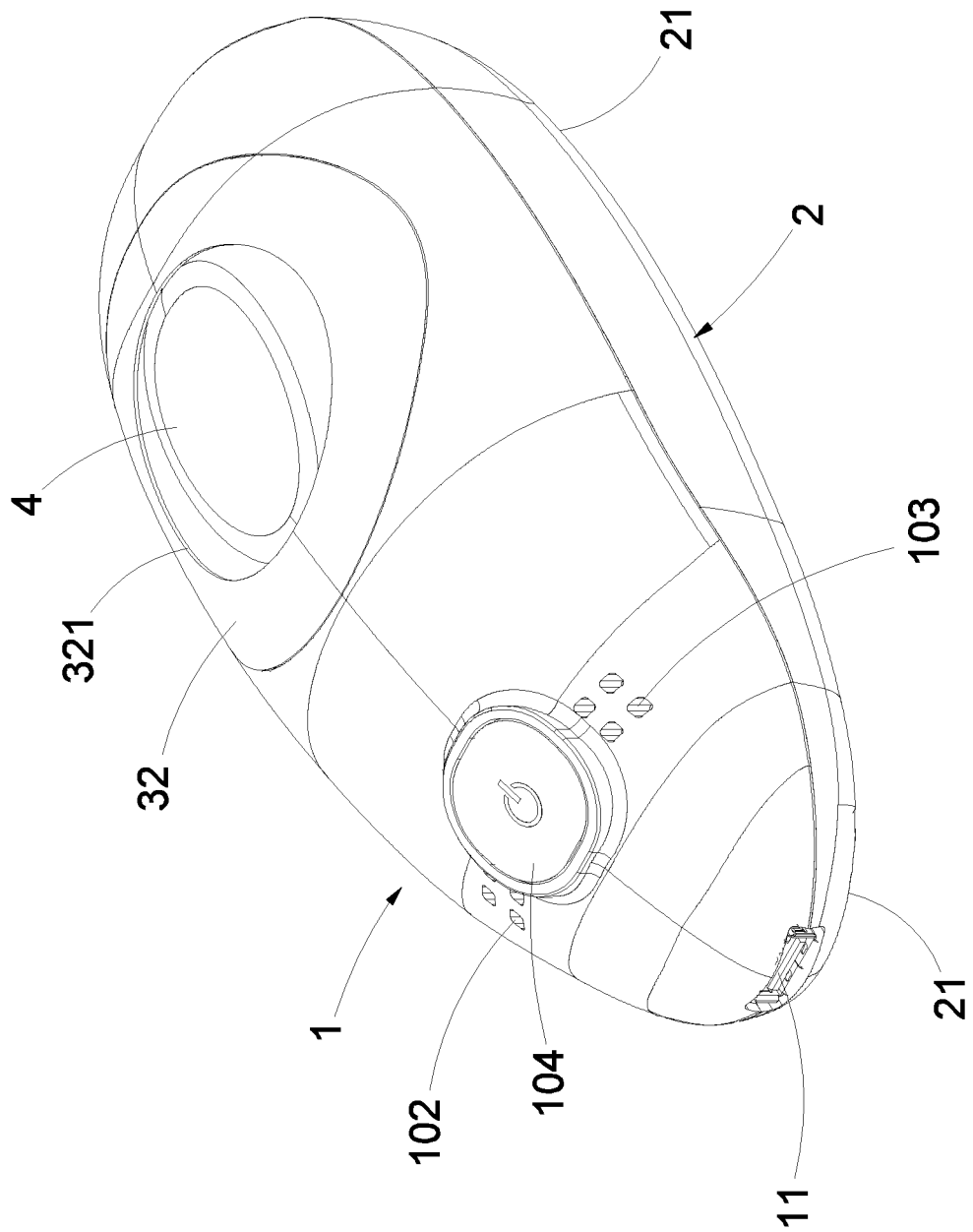
FIG. 2 is a perspective view showing the assembly according to the present invention.
Figure 3:
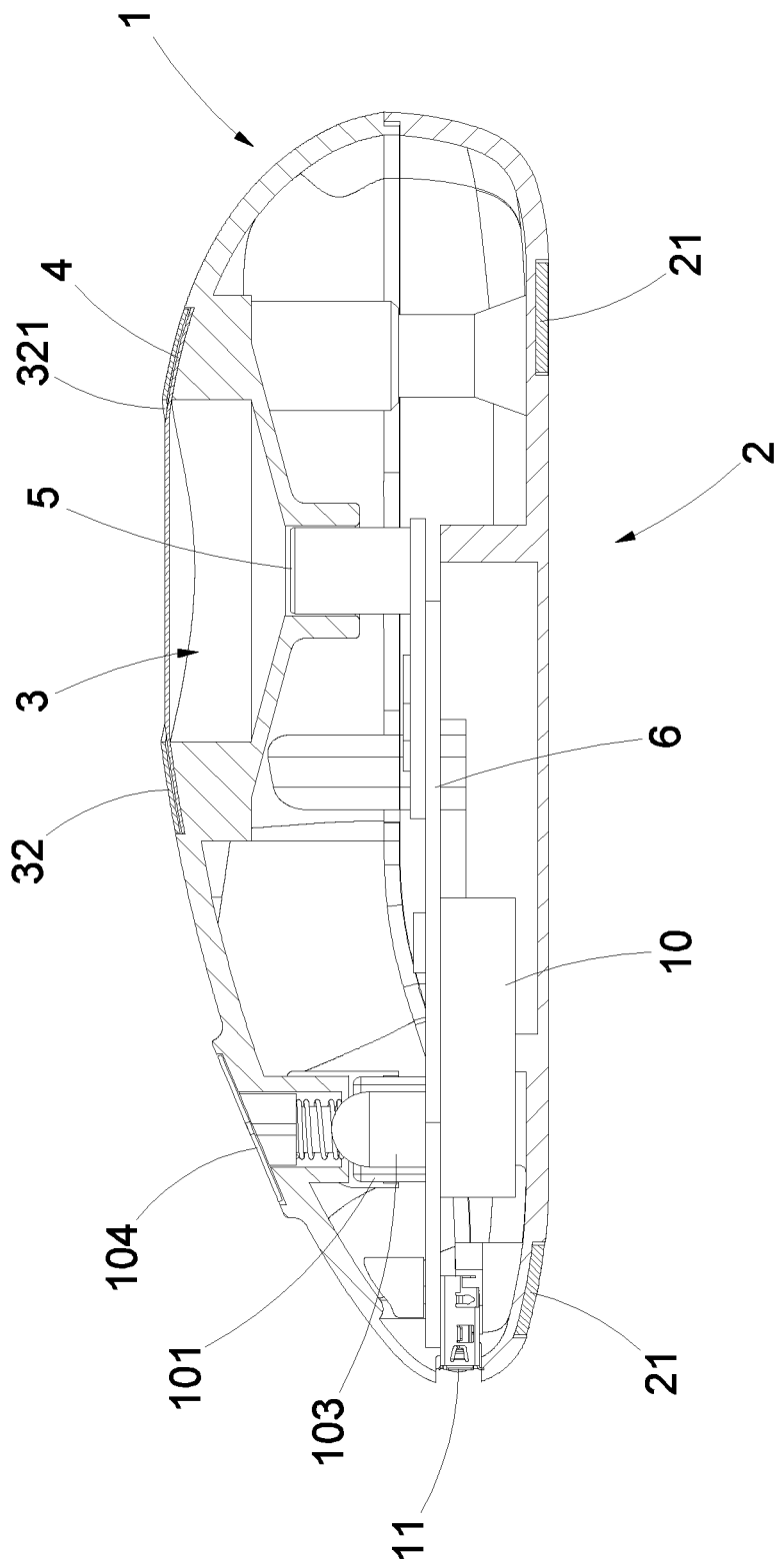
FIG. 3 is a cross sectional view showing the assembly according to the present invention.
Figure 4:
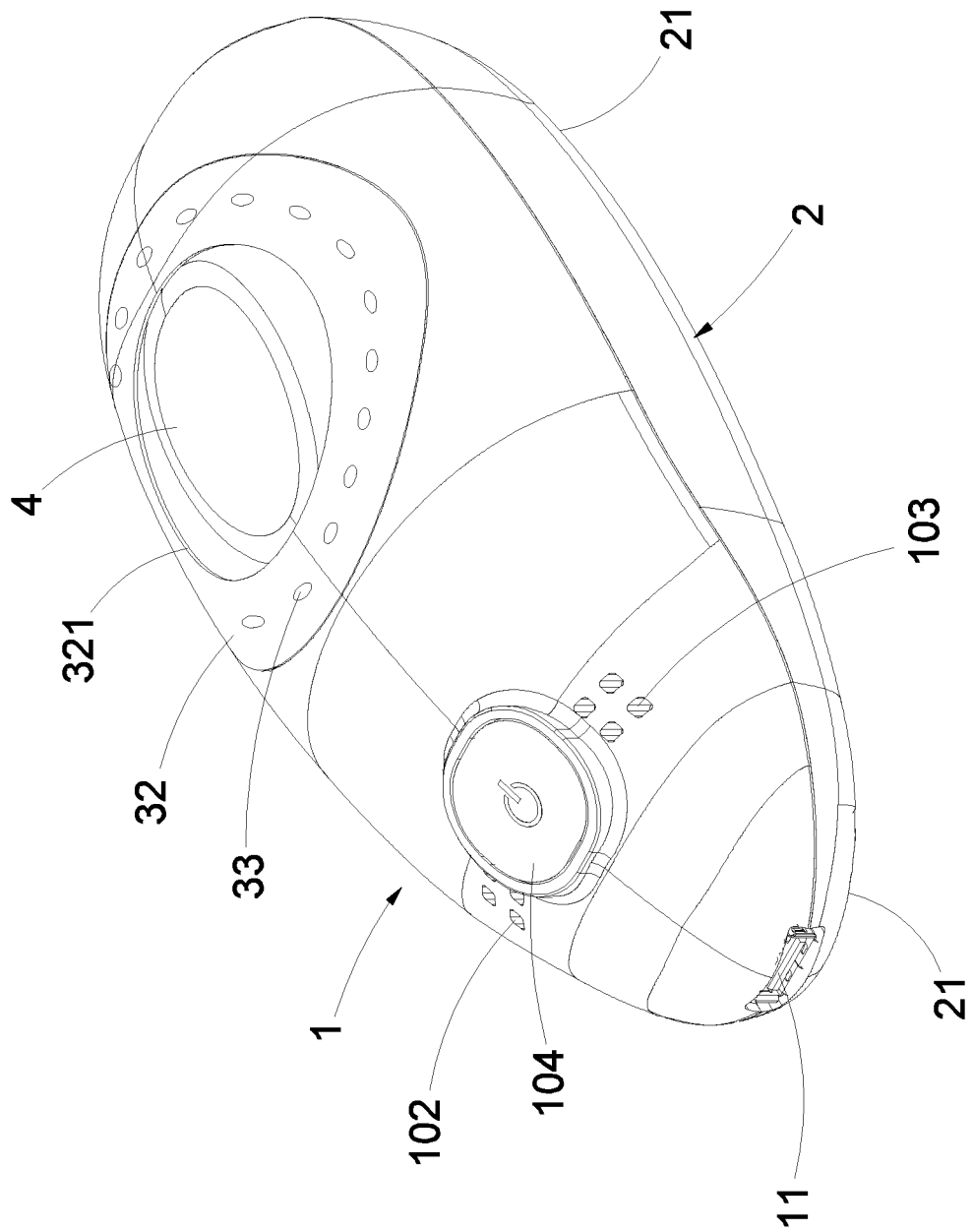
FIG. 4 is a schematic view showing the accessory unit being disposed at the top end of the support ring according to one embodiment of the present invention.
Figure 5:
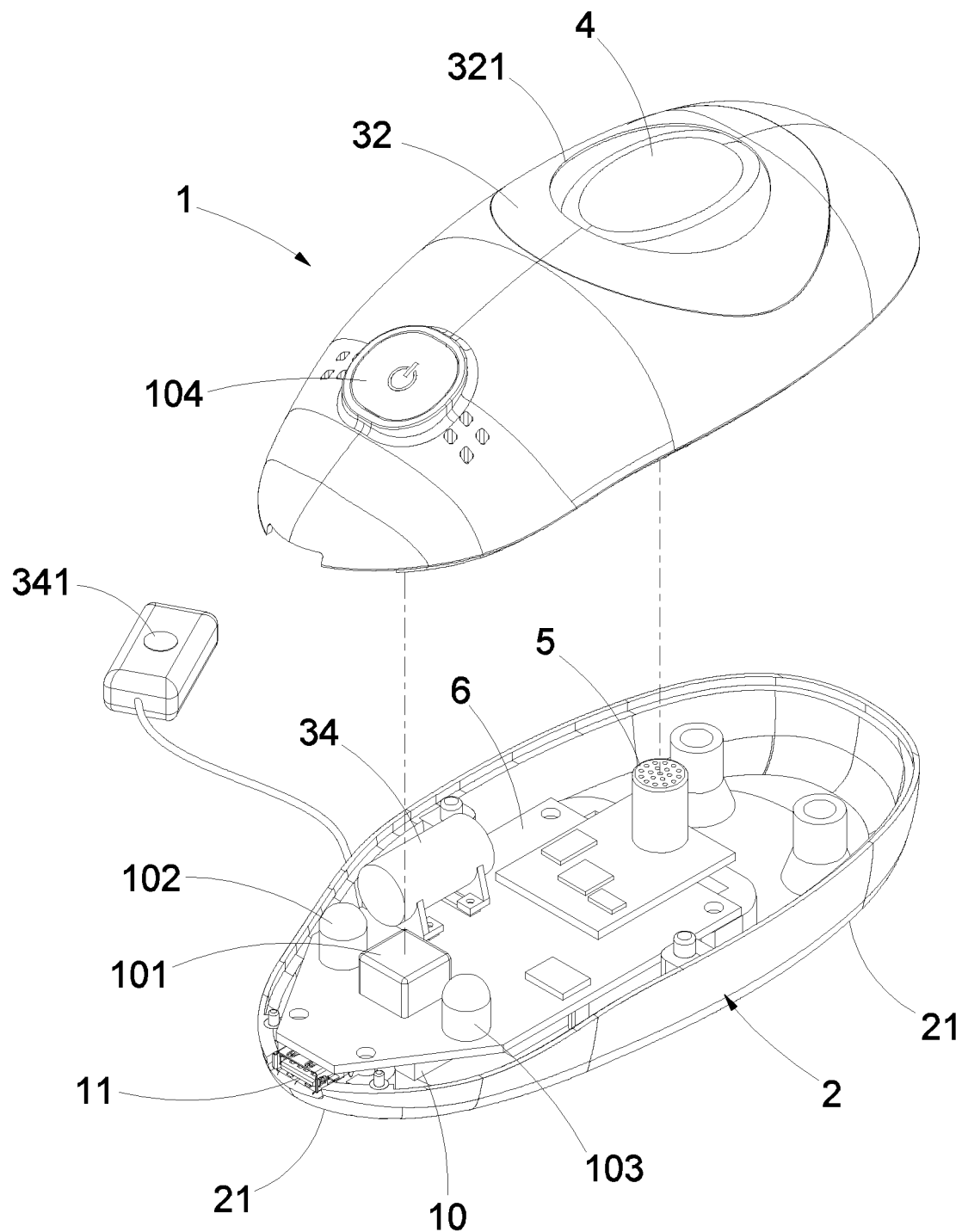
FIG. 5 is a schematic view showing the vibrating motor and the press button being disposed on the base seat according to one embodiment of the present invention.
Figure 6:
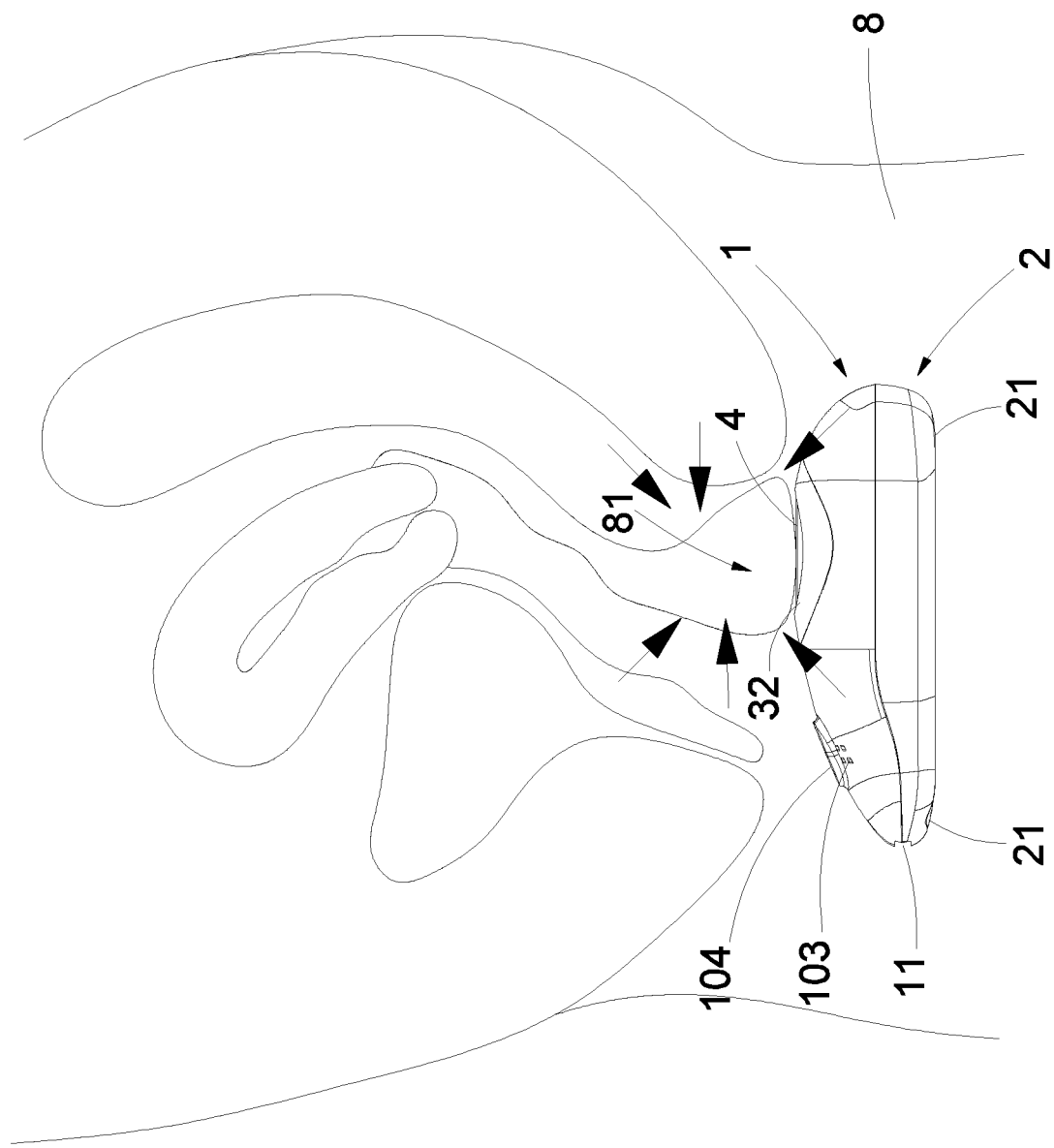
FIG. 6 is a schematic view showing the device of the present invention being interacting with the perineum according to one embodiment of the present invention.
Figure 7:
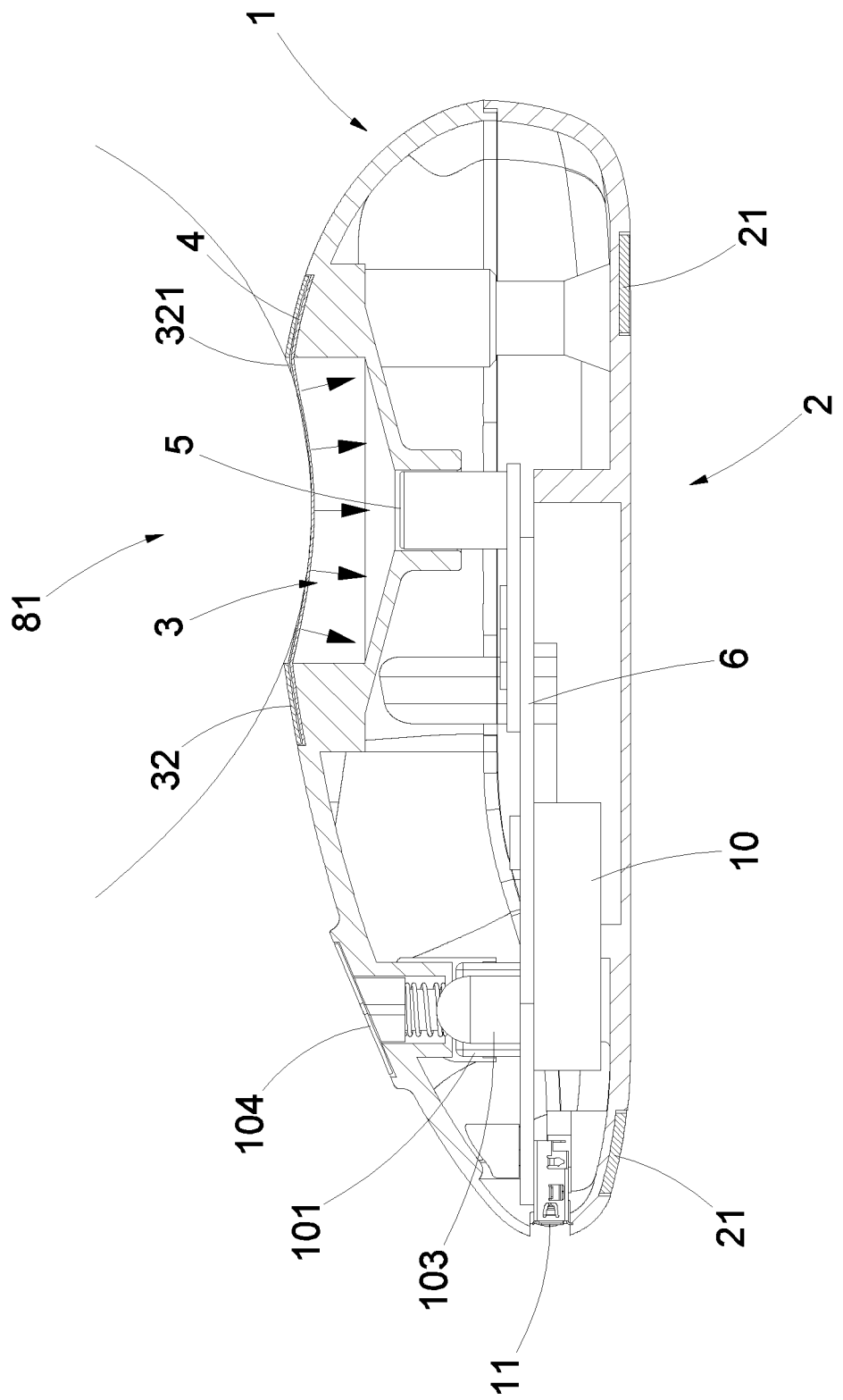
FIG. 7 is a schematic view showing the elastic sound receiving membrane being applied with the press of the skin muscle weight according to one embodiment of the present invention.
Figure 8:
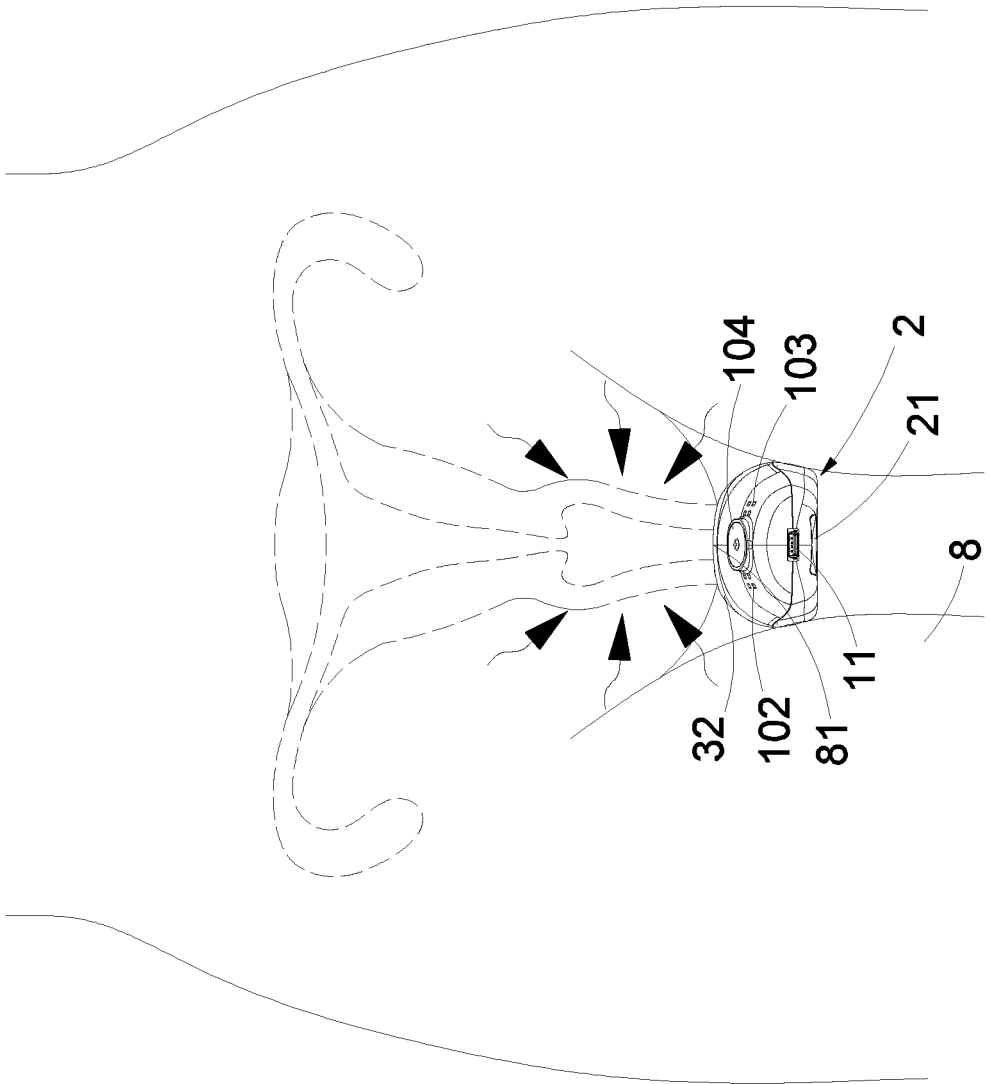
FIG. 8 is a schematic view showing the sound detecting device for pelvic floor muscle exercise being covered by the things according to one embodiment of the present invention.
Figure 9:
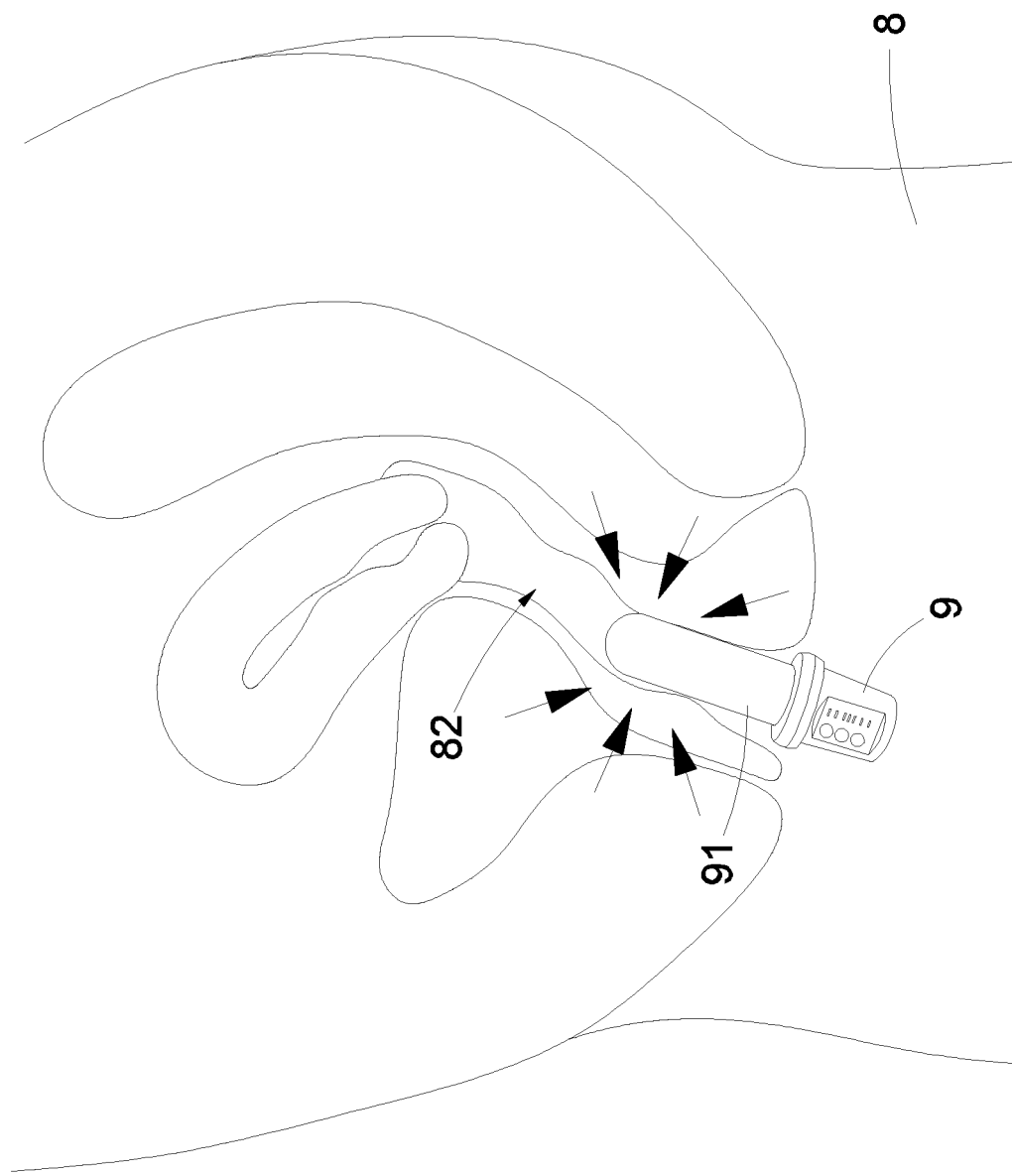
FIG. 9 is a schematic view showing an operating status of the conventional inserting type device.

Please refer from FIG. 1 to FIG. 8, wherein FIG. 1 is a perspective exploded view according to the present invention; FIG. 2 is a perspective view showing the assembly according to the present invention; FIG. 3 is a cross sectional view showing the assembly according to the present invention; FIG. 4 is a schematic view showing the accessory unit being disposed at the top end of the support ring according to one embodiment of the present invention; FIG. 5 is a schematic view showing the vibrating motor and the press button being disposed on the base seat according to one embodiment of the present invention; FIG. 6 is a schematic view showing the device of the present invention being interacting with the perineum according to one embodiment of the present invention; FIG. 7 is a schematic view showing the elastic sound receiving membrane being applied with the press of the skin muscle weight according to one embodiment of the present invention; and FIG. 8 is a schematic view showing the sound detecting device for pelvic floor muscle exercise being covered by the things according to one embodiment of the present invention. According to one preferred embodiment, the present invention provides a sound detecting device for pelvic floor muscle exercise, which is for applied to receive low frequencies generated when the pelvic floor muscle is relaxed and contracted, and includes: a main body 1, a sound collecting chamber 3, an elastic sound receiving membrane 4, a support ring 32, a microphone 5 and an electric circuit board 6.

A base seat 2 used for supporting is disposed in the main body 1, a bottom end of the base seat 2 of the main body 1 is disposed with at least one anti-skid sound isolating pad 21 used for avoiding displacements. Accordingly, the present invention can be fastened and not easy to be displaced, and an error generated through the sound caused by displacements can be prevented.

The sound collecting chamber 3 is disposed in the main body 1 and used for amplifying and collecting sounds for increasing the sensibility. An opening 31 having a sound receiving function is formed at a top end of the sound collecting chamber 3 (as shown in FIG. 1, FIG. 2 and FIG. 3).

The elastic sound receiving membrane 4 is disposed in the main body 1 and located at the opening 31 of the sound collecting chamber 3, the elastic sound receiving membrane 4 is used for covering on an outer skin layer or an outfit or a skirt where the lower frequencies generated when the pelvic floor muscle generates the relaxing or the contracting motions. The shape of the elastic sound receiving membrane 4 includes, but not limits to, an arc-shaped surface or a curved surface, and the material of which the elastic sound receiving membrane 4 is made is a soft material (as shown in FIG. 1, FIG. 2 and FIG. 3).

The support ring 32 is disposed at the top end of the main body 1, arranged at a periphery of the elastic sound receiving membrane 4 and corresponding to an outer periphery of the opening 31 of the sound collecting chamber 3; the center of the support ring 32 is formed with a middle hole 321 allowing the elastic sound receiving membrane 4 to be exposed, the material of which the support ring 32 is made includes, but not limits to, a metal material or a plastic material (as shown in FIG. 1, FIG. 2 and FIG. 3).

The microphone 5 is disposed at a bottom end of the sound collecting chamber 3 (as shown in FIG. 1, FIG. 2 and FIG. 3).

The electric circuit board 6 is disposed on the base seat 2 and used for providing a wave filtering function and an amplifying function; the electric circuit board 6 is connected to the microphone 5 and used for filtering high sound waves, middle sound waves and low sound waves so that the low frequencies generated when the pelvic floor muscle is relaxed or contacted can be individually kept. Moreover, the electric circuit board 6 can be used for providing a functional operating function and a received sound data transferring function through being connected to at least one smart device 7 installed with an application program (APP) 71 via a Bluetooth device (as shown in FIG. 1, FIG. 2 and FIG. 3). With the gravity of the outer skin muscle weight and the sound collecting chamber 3, the elastic sound receiving membrane 4 is able to descend to be tightly adjacent to the skin or the outfit or the skirt, thus the lower frequencies generated when the pelvic floor muscle vibrates can be amplified and precisely collected.

According to the present invention, the top end of the main body 1 is disposed with a charging light 102, a Bluetooth light 103, a switch light 104 and a power switch 101 which are connected to the electric circuit board 6; a charging hole 11 is formed for a purpose of charging electricity, at least one battery 10 connected to the electric circuit board 6 is disposed in the main body 1; when the battery 10 is electrically charged through the charging hole 11, the charging light 102 is able to emit lights; when the smart device 7 is connected to the Bluetooth device, the Bluetooth light 103 is able to emit lights; when being operated, the power switch 101 is pressed to allow the switch light 104 to emit lights.

Please refer to FIG. 4 and FIG. 5, according to the present invention, a top end of the support ring 32 is additionally disposed with at least one accessory unit 33 including, but not limiting to, an infrared unit or a magnet unit which is used for soothing the pelvic floor muscle and blood circulation (as shown in FIG. 4). According to the present invention, the base seat 2 is disposed with at least one vibrating motor 34 which enables the main body 1 to vibrate, massages the pelvic floor muscle and is connected to the electric circuit board 6, and at least one press button 341 used for controlling the vibrating motor 34 is disposed at an outer side of the main body 1 and connected to the electric circuit board 6 (as shown in FIG. 5).

Please refer to FIG. 6, FIG. 7 and FIG. 8, the shape of the main body 1 provided by the present invention includes, but not limits to, an oval shape or an enlarged status so as to be formed as a chair cushion; when a user is in a sitting status, regardless wearing the outfit or the skirt, for a long time (for example 5 to 10 minutes), the device provided by the present invention is disposed at a perineum 81 located between two thighs 8 of the user (as shown in FIG. 6), the perineum 81 is corresponding to the membrane of the elastic sound receiving membrane 4, and the sound collecting area can be enlarged to become a recessed three-dimensional sound collecting area through the weight of the skin muscle (as shown in FIG. 7), thus the vibrating low frequencies generated when the pelvic floor muscle is relaxed or contracted can be heard more clearly through reaching the deeper pelvic floor muscle layer; when the user does the Kegel sphincter exercises to train the muscle strength and the muscle endurance and the instant responsiveness of the pelvic floor muscle, the device provided by the present invention, which satisfies the ergonomics, is able to be directly and deeply positioned on the pelvic floor muscle, thus the device is prevented from being displaced and noises generated due to relative displacements between the device and cloth can be avoided, the structure of the elastic sound receiving membrane 4 can also isolate the muscle frequency of the thighs 8; when the pelvic floor muscle is contracted and relaxed to do the lifting anus and the pelvic floor muscle group exercises, the low frequencies generated when the pelvic floor muscle is contracted and relaxed can be received by the elastic sound receiving membrane 4 provided by the present invention without the needs of electrodes and being inserted into any human part (as shown in FIG. 8), when the elastic sound receiving membrane 4 is subjected to the downward pressing force of the skin muscle, the three-dimensional recessed surface is formed to increase the sound receiving area, in other words the three-dimensional recessed surface can receive more low frequencies generated by the pelvic floor muscle under the same cross section area, thus the detection is more precise and the received low frequencies of the pelvic floor muscle are provided to the electric circuit board 6 which is connected to the sound collecting chamber 3 and the microphone 5 used for amplifying and filtering waves.

According to the present invention, the interior and the top end of the main body 1 are respectively disposed with the base seat 2, the sound collecting chamber 3, the elastic sound receiving membrane 4, the support ring 32, the microphone 5 and the electric circuit board 6; as such, the elastic sound receiving membrane 4 is downwardly pressed through the pressure supplied by the skin muscle weight for being in a recessed status so as to be tightly adjacent to the outer side of the skin or the outfit or the skirt and the sound collecting chamber 3 is used for amplifying, thus the low frequencies generated through the vibrations caused by the pelvic floor muscle being contracted and relaxed can be collected with a more precise effect, and the Bluetooth device is used for transferring to the smart device 7 installed with the application program (APP) 71; moreover, the device provided by the present invention satisfies the ergonomics and can be conveniently operated without the needs of the electrodes and being inserted in the human part. Accordingly, the present invention is novel, more practical in use and satisfies the requirements of the users.

Based on what have been disclosed above, while this present invention has been described by means of specific embodiments, numerous modifications and variations could be made thereto by those skilled in the art without departing from the scope and spirit of the present invention set forth in the claims.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific examples of the embodiments disclosed and that modifications and other embodiments are intended to be included within the scope of the appended claims. Although specific terms are employed herein, they are used in a generic and descriptive sense only and not for purposes of limitation.

What is claimed is:

1. A sound detecting device for pelvic floor muscle exercise, applied to receive low frequencies generated when the pelvic floor muscle is relaxed and contracted, characterized in including:
    a main body, having a base seat disposed therein and used for supporting;
    a sound collecting chamber, disposed in the main body and used for amplifying and collecting sounds for increasing the sensibility, wherein an opening having a sound receiving function is formed at a top end of the sound collecting chamber;
    an elastic sound receiving membrane, disposed in the main body and located at the opening of the sound collecting chamber, wherein the elastic sound receiving membrane covers on at a desired detecting location of an outer skin layer or an outfit or a skirt where the lower frequencies generated when the pelvic floor muscle is relaxed or contracted;
    a support ring, disposed at a top end of the main body, arranged at a periphery of the elastic sound receiving membrane and corresponding to an outer periphery of the opening of the sound collecting chamber, wherein a center of the support ring is formed with a middle hole allowing the elastic sound receiving membrane to be exposed;
    a microphone, disposed at a bottom end of the sound collecting chamber; and
    an electric circuit board, disposed on the base seat, used for providing a wave filtering function and an amplifying function, and connected to the microphone;
    wherein, the elastic sound receiving membrane is downwardly pressed through a pressure supplied by the skin muscle weight for being in a recessed status so as to be tightly adjacent to the skin or the outfit or the skirt, thus the low frequencies generated through the vibrations caused by the pelvic floor muscle being contracted and relaxed are able to be amplified and precisely collected.

2. The sound detecting device for pelvic floor muscle exercise as claimed in claim 1, wherein a top end of the main body is disposed with a charging light, a Bluetooth light, a switch light and a power switch which are connected to the electric circuit board; a charging hole is formed for a purpose of charging electricity, at least one battery connected to the electric circuit board is disposed in the main body.

3. The sound detecting device for pelvic floor muscle exercise as claimed in claim 1, wherein a top end of the support ring is additionally disposed with at least one accessory unit including, but not limiting to, an infrared unit or a magnet unit which is used for soothing the pelvic floor muscle and blood circulation.

4. The sound detecting device for pelvic floor muscle exercise as claimed in claim 1, wherein the base seat is disposed with at least one vibrating motor which enables the main body to vibrate, massages the pelvic floor muscle and is connected to the electric circuit board, and at least one press button used for controlling the vibrating motor is disposed at an outer side of the main body and connected to the electric circuit board.

5. The sound detecting device for pelvic floor muscle exercise as claimed in claim 1, wherein a bottom end of the base seat of the main body is disposed with at least one anti-skid sound isolating pad used for avoiding displacements.

6. The sound detecting device for pelvic floor muscle exercise as claimed in claim 1, wherein a shape of the elastic sound receiving membrane includes, but not limits to, an arc-shaped surface or a curved surface.

7. The sound detecting device for pelvic floor muscle exercise as claimed in claim 1, wherein a material of which the elastic sound receiving membrane is made is a soft material.

8. The sound detecting device for pelvic floor muscle exercise as claimed in claim 1, a material of which the support ring is made includes, but not limits to, a metal material or a plastic material.

9. The sound detecting device for pelvic floor muscle exercise as claimed in claim 1, wherein the electric circuit board is used for providing a functional operating function and a received sound data transferring function through being connected to at least one smart device installed with an application program (APP) via a Bluetooth device.

\* \* \* \* \*